United States Patent
Deshpande et al.

(10) Patent No.: US 9,389,175 B2
(45) Date of Patent: Jul. 12, 2016

(54) DEVICE AND PROCESS TO APPROXIMATE SOMATIC CELL COUNT OF UNTREATED MAMMALIAN MILK

(71) Applicant: Satish Deshpande, Guelph (CA)

(72) Inventors: Satish Deshpande, Guelph (CA); Donald F Moyer, Chicago, IL (US)

(73) Assignee: DESHPANDE, Satish, Guelph (CA)

( * ) Notice: Subject to any disclaimer, the term of this patent is extended or adjusted under 35 U.S.C. 154(b) by 0 days.

(21) Appl. No.: 14/085,004

(22) Filed: Nov. 20, 2013

(65) Prior Publication Data

US 2014/0139834 A1     May 22, 2014

Related U.S. Application Data

(60) Provisional application No. 61/728,740, filed on Nov. 20, 2012.

(51) Int. Cl.
  *G01N 21/00* (2006.01)
  *G01N 21/51* (2006.01)
  *G01N 21/47* (2006.01)

(52) U.S. Cl.
  CPC ........ *G01N 21/51* (2013.01); *G01N 2021/4707* (2013.01)

(58) Field of Classification Search
  CPC ....... G01N 21/51; G01N 21/00; G01N 33/48; G01N 33/00; A01J 33/00
  See application file for complete search history.

(56) References Cited

U.S. PATENT DOCUMENTS

| | | | |
|---|---|---|---|
| 6,315,955 B1 * | 11/2001 | Klein | 422/73 |
| 6,710,879 B1 * | 3/2004 | Hansen et al. | 356/436 |
| 2006/0124064 A1 * | 6/2006 | Fullam et al. | 119/14.02 |

* cited by examiner

*Primary Examiner* — Tarifur Chowdhury
*Assistant Examiner* — Jamil Ahmed
(74) *Attorney, Agent, or Firm* — Gowling WLG (Canada) LLP; Jeffrey W. Wong

(57) ABSTRACT

Device and process to approximate somatic cell count (SCC) of untreated mammalian milk by the two variable equation SCC=f(FSL, FAT) with a forward scattered light factor (FSL) being obtained by detecting light scattered by the milk into an angular range within, and less than, the angular range 0.0 to 0.5 degrees away from the central axis of incident light, with a proxy (FAT) for the fat content of the milk, which may be obtained by detecting light attenuation of the milk sample, and with the function (f) being obtained by calibration of the device using reference milk samples.

7 Claims, 4 Drawing Sheets

| Sample | FSL | FAT | SCC FC | SCC from Equation | % Error |
|---|---|---|---|---|---|
| 1 | 128.5 | 1884 | 96 | 55 | -42.7 |
| 2 | 117.5 | 2495.3 | 121 | 153 | 26.4 |
| 3 | 126.5 | 2366.6 | 133 | 156 | 17.3 |
| 4 | 122.7 | 2318.2 | 150 | 132 | -12.0 |
| 5 | 117.4 | 2670 | 174 | 192 | 10.3 |
| 6 | 139.9 | 2422.3 | 205 | 215 | 4.9 |
| 7 | 138.5 | 2512.1 | 240 | 230 | -4.2 |
| 8 | 162.7 | 2631.8 | 284 | 293 | 3.2 |
| 9 | 156.2 | 2702.1 | 325 | 334 | 2.8 |
| 10 | 151.9 | 2804.4 | 421 | 411 | -2.4 |
| 11 | 204.4 | 2754.3 | 505 | 513 | 1.6 |
| 12 | 224.7 | 2668.3 | 560 | 564 | 0.7 |
| 13 | 227.9 | 2743.2 | 600 | 592 | -1.3 |
| 14 | 245.7 | 2846.7 | 670 | 677 | 1.0 |

$$SCC = -811.016 + 0.223*FAT + 3.472*FSL$$

The equation was obtained using the regression tool of SigmaPlot$^{tm}$ with milk samples 1, 2, 3, 5, 8, 10 above and two other milk samples providing the reference data for the regression tool.

FSL values are the sum of detected forward scattered light data from nine pixels, four behind a beam block and five beyond the beam block.

FAT values are proxies for fat content obtained by detecting light attenuation of the milk samples.

SCC FC values are standard flow cytometry measurements.

Values in the "percent error" column were obtained by subtracting the SCC FC values from the SCC values obtained by the equation and dividing by the SCC FC values and multiplying by 100.

FIG 2

DEVICE AND PROCESS TO APPROXIMATE SOMATIC CELL COUNT OF UNTREATED MAMMALIAN MILK

This application claims priority of U.S. provisional application 61/728,740 filed 20 Nov. 2012 which is incorporated in full herein by reference.

SUMMARY

It is a new result and unexpected discovery that somatic cell count (SCC) of untreated mammalian milk can 1) be sensitively, reliably, and usefully approximated by the two variable equation SCC=f (FSL, FAT) with 2) a forward scattered light factor (FSL) being obtained by detecting light scattered by the milk into an angular range within, and less than, the angular range 0.0 to 0.5 degrees away from the central axis of incident light, with 3) a proxy (FAT) for the fat content of the milk being obtained by detecting light attenuation of the milk sample, and with 4) the function (f) being obtained by calibration of the device using reference milk samples.

Detecting the forward scattered light can be done in line in normal milking systems which are changed only by passage of normally flowing milk through the device after normal filtering. No added markers are needed; no changes in milk contents or concentrations are needed.

The new result and unexpected discoveries listed above can be obtained when incident light, a forward scattered light detector, and a path length through a milk sample in the sample container of incident light through the normally flowing milk are configured together so that stochastic fluctuations of orientations of electric dipole moments of somatic cells in an ensemble of mammalian somatic cells in the milk sample add incident light scattered by the ensemble into a first forward scattered light peak angular range having a greatest intensity at a first forward scattered light peak angle away from the incident light central axis.

BRIEF DESCRIPTION OF THE DRAWINGS

FIG. 2 shows some illustrative numerical data and shows an option for approximating somatic cell count.

DETAILED DESCRIPTION

The critical need for sensitive and reliable approximation of somatic cell count is well described in a report "Premiums, Production and Pails of Discarded Milk: How Much Money Does Mastitis Cost You?" by Pamela Ruegg, DVM, MPVM, University of Wisconsin, Madison. Part of her first paragraph is quoted here with her references interpolated in square brackets: "Profit centered dairy farms strive to maximize milk price and control costs. One way to control costs is by minimizing the rate of disease. The most costly disease of dairy cattle is generally considered to be mastitis. Mastitis can cause both clinical and subclinical disease. On many farms, subclinical mastitis is the most economically important type of mastitis because of the long-term effect of chronic infections on total milk yields. Persistent long-term infections with contagious pathogens (such as *Strep agalactia* and *Staph aureus*) damage milk secretory cells and result in reduced milk production. [White G C. Couture, G W., Anderson E O et al, 1937. 'Chronic bovine mastitis and milk yield.' J Dairy Sci 20:171-180] A recent study estimated that the cost of subclinical mastitis to the US dairy industry exceeds $1 billion annually. [Ott, S. 'Costs of herd-level production losses associated with subclinical mastitis in US Dairy Cows.' 1999. PP 152-156 in Proceedings of the 38th annual meeting of National Mastitis Council, Arlington Va. Natl. Mast Coun. Madison Wis.] The effect of subclinical mastitis is shown in the somatic cell count (SCC) at the individual cow level and ultimately in the bulk tank. The SCC of cows infected with subclinical mastitis rises as the cows immune system sends white blood cells to the udder to fight off mastitis pathogens."

Figure 1:
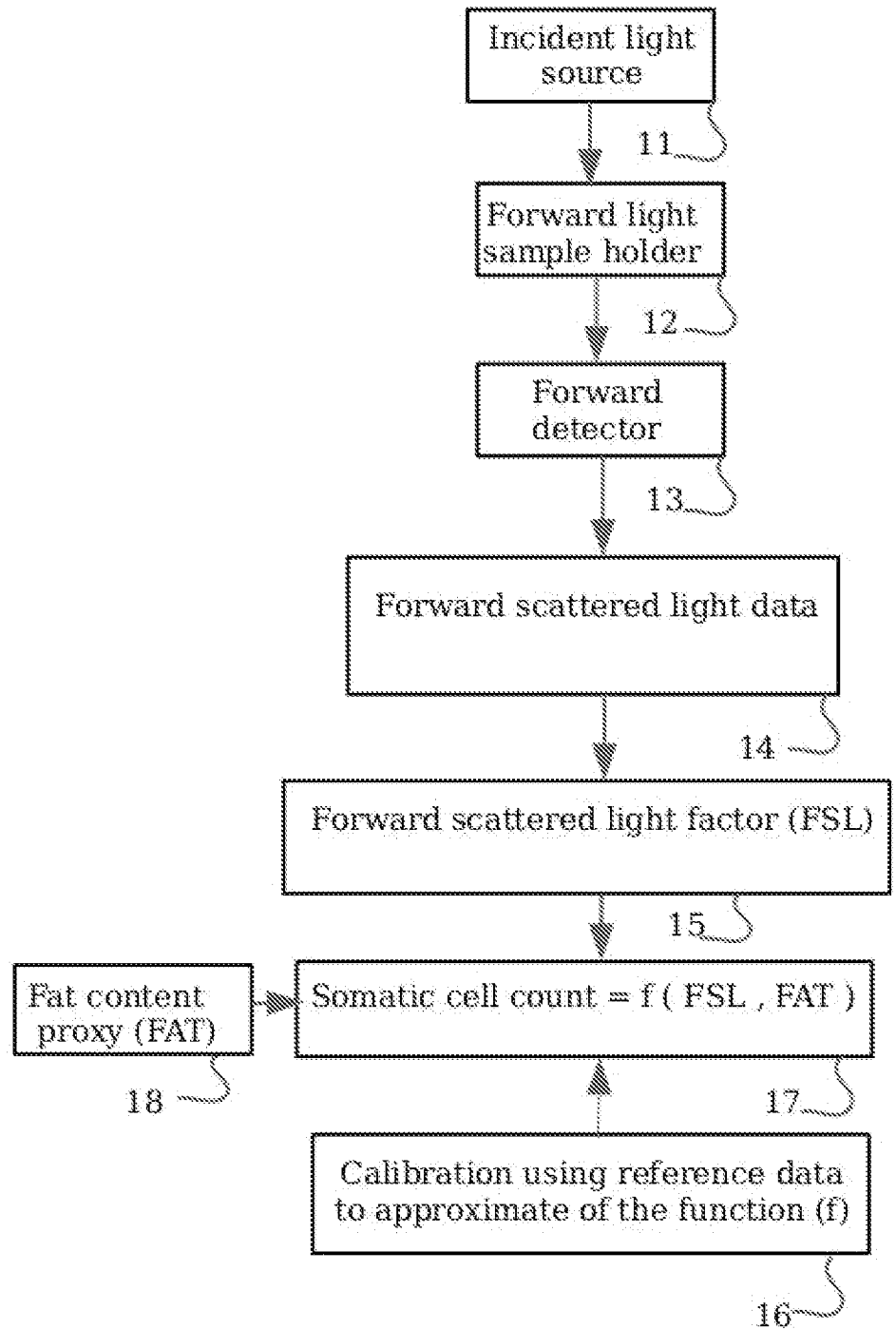
FIG. 1 illustrates parts of an option for the device and process.

FIG. 1 shows parts of one option for the device and process to approximate somatic cell count of untreated mammalian milk. The device comprises a source of incident light 11, the incident light having an incident light central axis; a forward scattered light detector 13, the forward scattered light detector being intersected by the incident light central axis; a sample container 12 to contain milk samples, the sample container being traversed by the incident light central axis so that the incident light central axis has a path length through a milk sample in the sample container through a milk sample in the sample container prior to forward scattered light detection by the forward scattered light detector.

The device also comprises configuration together of incident light, the forward scattered light detector, and the path length through the milk sample in the sample container so that stochastic fluctuations of orientations of electric dipole moments of somatic cells in an ensemble of mammalian somatic cells along the path length through the milk sample in the sample container add incident light scattered by the ensemble into a first forward scattered light peak angular range having a greatest intensity at a first forward scattered light peak angle away from the incident light central axis.

The science of light scattering by ensembles of scatterers, which is well known to persons having ordinary skill in this art, is detailed in the book: Bruce J. Berne, Robert Pecora, *Dynamic Light Scattering: With Applications to Chemistry, Biology, and Physics*, Wiley, 1976 and Courier Dover Publications, 2000.

The path length through a milk sample in the sample container must be long enough to satisfy those ensemble scattering conditions, not so long that multiple scattering obscures the data, and short enough so that the fat content of the milk does not obscure the data. A two millimeter path length through a milk sample in the sample container works well. A 780 nm 25 mW laser with a 0.8 mm beam diameter works well. A quartz cuvette 8 mm by 12 mm by 2 mm (the path length through a milk sample in the sample container) with a milk flow rate of 10 mL/min works well. A Logitech C160 web camera with USB interface exposing 15 frames per second for 30 seconds works well for detection of forward scattered light data.

With the milk flowing over the time of the exposures problems due to fat separation are reduced. Fat separation problems are also reduced by higher exposure rates.

These choices work well for bovine milk in the somatic cell count range above 150,000 somatic cells per ml. Milk from other animals and other somatic cell count ranges can work well with other choices.

The device also comprises detection of forward scattered light data 14 over a detection angular range including at least part of the first forward scattered light peak angular range.

The device also comprises a detected forward scattered light factor (FSL) 15 obtained using at least one datum from detected forward scattered light data.

It is part of the unexpected discovery here that the somatic cell count 17 is a function of this detected forward scattered light factor and at least a proxy (FAT) for fat content 18 of the milk with the function being approximated by calibration 16 of the device.

The fat content variable (FAT) could be fat content obtained from standard measurements. The fat content variable can be obtained in many and various ways. It is part of the unexpected discoveries here that attenuation of light by the milk sample can be used as a proxy (FAT) for the fat content variable.

Any part, and alternatively parts, of the first forward scattered light angular range can comprise detected forward scattered light data. Any part, and alternatively any parts, of detected forward scattered light data can be used to obtain a detected forward scattered light factor. The detected forward scattered light factor can be obtained by any of various calculations using detected forward scattered light data.

It is part of the unexpected discovery here that summing values of detected forward scattered light data in an angular range within, and less than, the angular range 0.0 to 0.5 degrees away from the incident light central axis provides a detected forward scattered light factor (FSL) which with at least a fat content proxy (FAT) and calibration of the device, can be used to reliably, sensitively, and usefully approximate somatic cell count.

Forward scattered light data can be detected in an angular range greater than 0.0 to 0.5 degrees away from the incident light central axis and can be obtained from several angular ranges.

As an option the detected forward scattered light factor can be obtained from the detected forward scattered light data remote from the forward scattered light detector. This could be done by a smartphone application for example.

The forward scattered light detector can be any light sensitive detector which can detect forward scattered light at least one angle, and alternatively at a pre-determined set of angles, in the first forward scattered light peak angular range. For example, the forward scattered light detector can be a cmos detector and alternatively a ccd detector.

To obtain the detected forward scattered light factor a forward scattered light detector can be configured to directly output the value of forward scattered light detected at a single angle and alternatively directly output various combinations of values of forward scattered light detected at a pre-determined set of angles.

It is a part of the unexpected discovery here that the device can be calibrated using reference data obtained from reference milk samples to approximate the function (f) for the equation SCC=f (FSL, FAT). Each of the reference milk samples has a known fat content, which at least can be represented by a proxy (FAT) such as light attenuation. Each of the reference milk samples has a known somatic cell content (SCC) which can be obtained from standard flow cytometry measurements. For each of the reference milk samples the detected forward scattered light factor (FSL) is obtained from the detected forward scattered light data obtained from the sample.

Small details of the configuration of a specific device change the function (f) so each device is calibrated using reference data. And, since small details of the configuration of a device can change with time, the function (f) will change with time.

As an option the device can also comprise approximation of somatic cell content of the milk sample 17 using the equation $$SCC_t = f(FAT_t, FSL_t)$$

with ($SCC_t$) approximating somatic cell count of a test milk sample, with ($FSL_t$) comprising the detected forward scattered light factor of the test milk sample, with ($FAT_t$) representing fat content of the test milk sample, with (f) comprising a function obtained by calibration of the device 16 using reference data comprising:

detected forward scattered light factors (FSL) obtained from each set of detected forward scattered light data detected for n reference milk samples with the index r running from 1 to n, representations of fat content ($FAT_r$) of each of the n reference milk samples, and known somatic cell counts ($SCC_r$) of each the n reference milk samples.

As an option the device can also comprise approximation of somatic cell count remote from the forward scattered light detector. This could be done by a smartphone application for example.

FIG. 2 shows illustrative numerical data for fourteen specific milk samples.

In the illustrative example of FIG. 2 the detected forward scattered light factors (FSL) are each the sum of detected forward scattered light data from nine pixels, four behind a beam block which blocks direct transmission of the incident light and five beyond the beam block which corresponds to an angular range within, and less than, the angular range 0.0 to 0.5 degrees away from the incident light central axis. (A beam block is the easy way—among many ways—to avoid problems due to the high intensity of direct transmission of the incident light.)

Attenuation of 468 nm true blue LED light incident along an attenuation path through the milk sample was used as a proxy (FAT) for the fat content.

Somatic cell count results (SCC FC) were obtained by standard flow cytometry measurements.

Six milk samples (1, 2, 3, 5, 8, 10) of the fourteen milk samples and two other milk samples were used as the reference milk samples. The reference data are from the columns FSL, FAT, and SCC FC. The reference data and the regression tool of SigmaPlot™ were used to approximate the equation for somatic cell count SCC shown in FIG. 2:

$$SCC = -811.016 + 0.223*FAT + 3.472*FSL$$

Values in the percent error column were obtained by subtracting the SCC FC values from the values obtained by the equation, dividing by the SCC FC values, and multiplying by 100.

Figure 3:
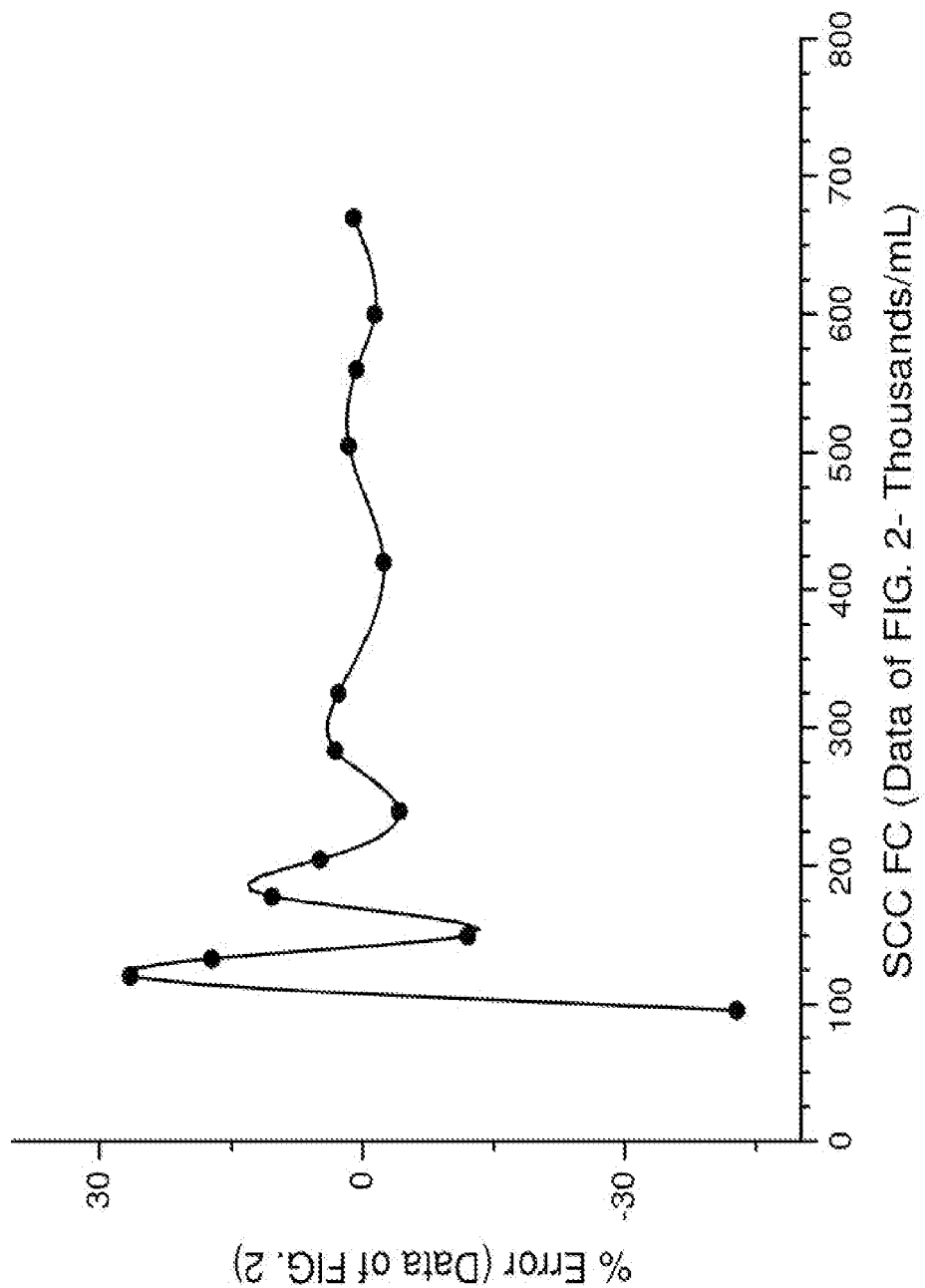
FIG. 3 shows the percent error between somatic cell count results obtained by the approximation of FIG. 2 and somatic cell count results obtained by standard flow cytometry measurements.

FIG. 3 shows percent error for somatic cell count results obtained by the equation shown in FIG. 2 plotted relative to the somatic cell count results obtained by the flow cytometry measurements. The equation works best in the range of greatest interest above 150,000 somatic cells per ml. Better results in the low Somatic cell count range can be obtained by providing a second shorter path length through a milk sample in the sample container.

As an option the path length through a milk sample in the sample container can comprise a first path length through a milk sample in the sample container and a second path length through the milk sample in the sample container not equal to the first path length through the milk sample in the sample container. A sample container with a first path length through the milk sample in the sample container and a second path length through the milk sample in the sample container can be moved so that the incident light and detector are alternately aligned with the first path length through the milk sample in the sample container and the second path length through the milk sample in the sample container.

Figure 4:
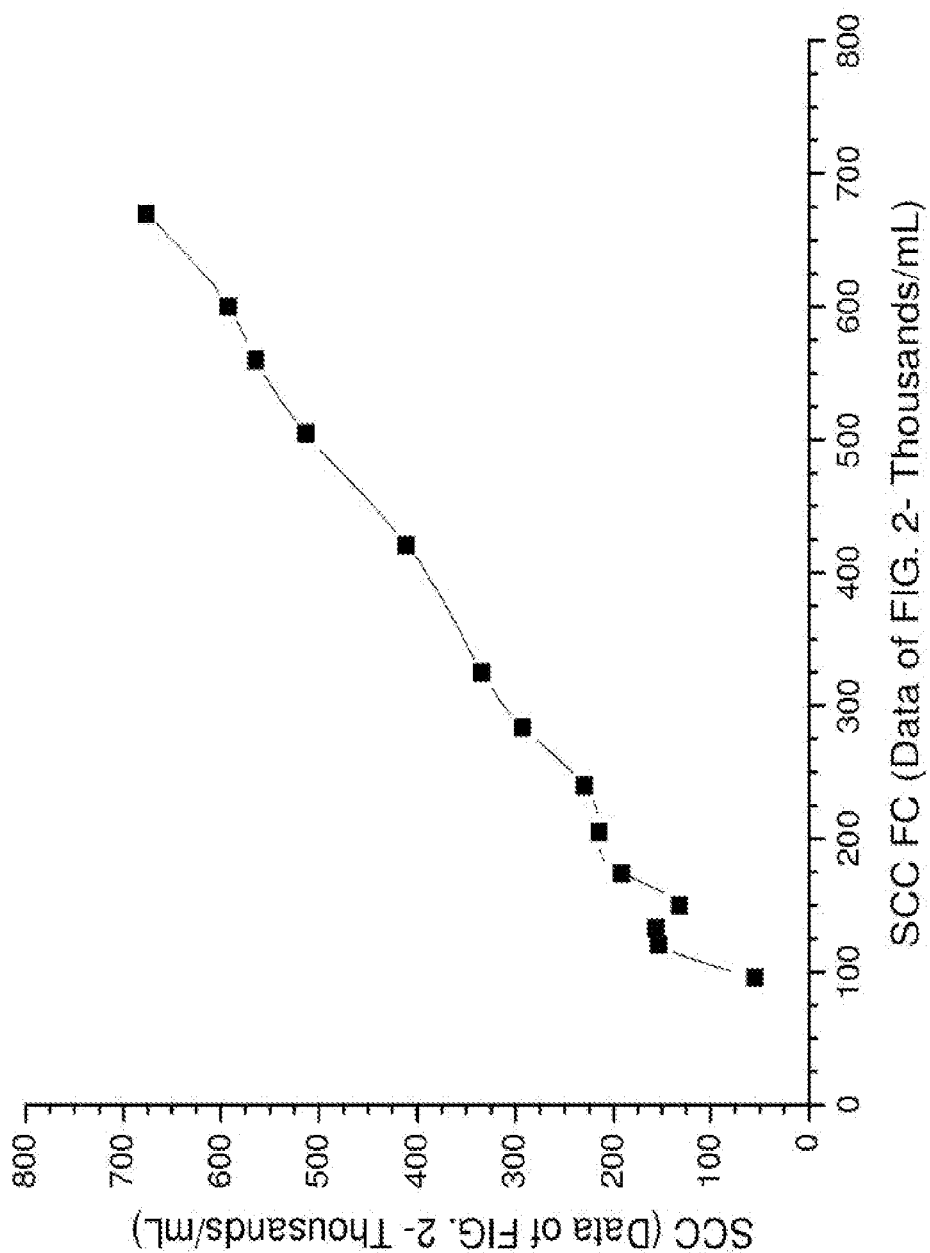
FIG. 4 also illustrates correspondence between the approximation results and the standard results.

FIG. 4 also shows how somatic cell count results obtained by the equation shown in FIG. 2 correspond to the somatic cell count results obtained by standard flow cytometry results.

The equation used in this example would improve to yield more accurate results if more reference milk samples and thus more reference data were included. It is part of the unexpected discovery here that an equation of the form SCC=a+b*FSL+c*FAT provides reliable, sensitive, and useful results in the somatic cell count range of greatest interest (coefficients a, b, and c being constants depending on details of a specific device and being determined by calibration of the specific device).

Many other ways to approximate an equation from reference data are possible. Other forms of an equation which can provide reliable, sensitive, and useful results in a specific somatic cell count range and for a specific configuration of devices are possible. Ordering reference data in look-up tables can be used to approximate somatic cell count.

There are many equivalent ways to obtain and use the data like the data illustrated in FIG. 2 so long as the incident light, the forward scattered light detector, and the path length through a milk sample in the sample container are configured together so that stochastic fluctuations of orientations of electric dipole moments of somatic cells in an ensemble of mammalian somatic cells along the path length through the milk sample in the sample container add incident light scattered by the ensemble into a first forward scattered light peak angular range having a greatest intensity at a first forward scattered light peak angle away from the incident light central axis and detection of forward scattered light data is obtained over a detection angular range including at least part of the first forward scattered light peak angular range.

This configuration can change to match a specific somatic cell count range. The configuration can change to match characteristics of milk from different kinds of animals.

Detected forward scattered light data and the detected forward scattered light factor can be expressed in arbitrary units so long as the same units are used in the reference data and in the approximation.

The fat content variable (FAT) could be fat content obtained from standard measurements. The fat content variable (FAT) can be obtained in various ways. Fat content can be expressed in arbitrary units so long as the same units are used in the reference data and in the approximation.

Approximation of somatic cell count can be limited to determination if the somatic cell count is at a pre-set value and alternatively below the pre-set value and alternatively above the pre-set value.

As an option the device can also comprise having the sample container be part of a system with continuous flow of milk. Approximation of somatic cell count can trigger a system for rerouting milk for a different use when the approximation determines that the milk has a somatic cell count at a pre-set value and alternatively below the pre-set value and alternatively above the pre-set value.

The invention claimed is:

1. A system to approximate somatic cell count of untreated mammalian milk, the system comprising:
    a source of incident light, the incident light having an incident light central axis;
    a forward scattered light detector, the forward scattered light detector being intersected by the incident light central axis;
    a sample container containing an untreated milk sample with white blood cells, the sample container between the source of incident light and the forward scattered light detector such that the incident light central axis passes through the untreated milk sample in the sample container to produce an incident light path length prior to being detected by the forward scattered light detector,
    whereby scattering of the incident light by white blood cells along the path length produces an elastic scattered peak bracketed by a narrowly forward angular range,
    thereby producing a greatest intensity of the elastic scattering peak being at a scattered light peak angle away from the incident light central axis;
    thereby producing a range of intensities of incident light as a function of angles away from the incident light central axis over at least part of the narrowly forward angular range, the range of intensities including a peak detection of the scattered peak:
    whereby the peak detection includes an angle detection of the scattered light peak angle; and
    a processor for calculating a forward scattered light factor (FSL) which includes the angle detection of the scattered light peak angle and at least one datum from the range of intensities for approximating the somatic cell count of the milk sample.

2. The system of claim 1 wherein the sample container is part of a milk collection system.

3. The system of claim 1 wherein the FSL is obtained remotely from the forward scattered light detector.

4. The system of claim 1 wherein the approximation of somatic cell content of the milk sample is calculated using SCC=f(FAT,FSL)
    where SCC represents the approximation of somatic cell count of the milk sample;
    where FSL represents the forward scattered light factor;
    where FAT represents a fat content of the milk sample; and
    where f represents a function obtained by a calibration of the system using reference data including:
    forward scattered light factors (FSLr) for n reference milk samples with an index (r) from 1 to n, with each value (FSLr) being interchangeable with the FSL,
    representations of fat content (FATr) of each of the n reference milk samples, and
    known somatic cell counts (SCCr) of each the n reference milk samples.

5. The system of claim 1 with the approximation calculated remotely from the forward scattered light detector.

6. The system of claim 1 wherein the path length comprises:
    a first path length component; and
    a second path length component not equal to the first path length component.

7. A system to approximate somatic cell count of mammalian milk sample, the system comprising:
    an incident light source for producing an incident light having a central axis;
    a forward scattered light detector, the forward scattered light detector being intersected by the central axis;
    a container for holding an untreated raw milk sample, the container holding the untreated raw milk sample being located between the incident light source and the forward scattered light detector, whereby the incident light passes through the container prior to being detected by the forward scattered light detector;

wherein the incident light is scattered by white blood cells within the untreated raw milk sample producing an angle scattering peak, detected by the forward scattered light detector, bracketed by a narrowly forward angular range such that a greatest intensity of the scattering peak is an angle away from the central axis;

wherein a set of intensity values are obtained, the set of intensity values representing an intensity of the incident light as a function of angle with respect to the central axis over at least part of the narrowly forward angular range, each set of intensity values including a peak detection of the angle scattering peak and a determination of a forward scattered light factor (FSL); the FSL based on the angle scattering peak and at least one datum;

wherein FSL is used for approximating the somatic cell count of the milk sample.

* * * * *